US00PP20188P2

(12) United States Plant Patent
de Koning

(10) Patent No.: US PP20,188 P2
(45) Date of Patent: Jul. 28, 2009

(54) *PAPAVER* PLANT NAMED 'PARADISO'

(50) Latin Name: *Papaver orientale*
Varietal Denomination: Paradiso

(75) Inventor: Eleonore de Koning, Boisyvon (FR)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 12/214,215

(22) Filed: Jun. 16, 2008

(51) Int. Cl.
*A01H 5/00* (2006.01)

(52) U.S. Cl. ..... Plt./464

(58) Field of Classification Search ..... Plt./464
See application file for complete search history.

*Primary Examiner*—Annette H Para
(74) *Attorney, Agent, or Firm*—C. A. Whealy

(57) ABSTRACT

A new and distinct cultivar of *Papaver* plant named 'Paradiso', characterized by its upright plant habit; moderately vigorous growth habit; large flowers with deep pink-colored petals with dark red-colored centers; and strong flowering stems.

2 Drawing Sheets

Botanical designation: *Papaver orientale.*
Cultivar denomination: 'PARADISO'.

BACKGROUND OF THE INVENTION

The present invention relates to a new and distinct cultivar of *Papaver,* botanically known as *Papaver orientale* and hereinafter referred to by the name 'Paradiso'.

The new *Papaver* originated from a cross-pollination of two unnamed selections of *Papaver orientale,* not patented. The new *Papaver* was discovered and selected by the Inventor as a single flowering plant from within the progeny of the stated cross-pollination grown in a controlled greenhouse environment in Oudelande, The Netherlands in May, 2004.

Asexual reproduction of the new cultivar by divisions since 2005 in Oudelande, The Netherlands has shown that the unique features of this new *Papaver* are stable and reproduced true to type in successive generations.

SUMMARY OF THE INVENTION

Plants of the cultivar Paradiso have not been observed under all possible environmental conditions. The phenotype may vary somewhat with variations in environment such as temperature and light intensity without, however, any variance in genotype.

The following traits have been repeatedly observed and are determined to be the unique characteristics of 'Paradiso'. These characteristics in combination distinguish 'Paradiso' as a new and distinct cultivar of *Papaver*:

1. Upright plant habit.
2. Moderately vigorous growth habit.
3. Large flowers with deep pink-colored petals with dark red-colored centers.
4. Strong flowering stems.

Plants of the cultivar Paradiso differ from plants of the parent selections primarily in flower color and plant height.

Plants of the new *Papaver* can be compared to plants of *Papaver orientalis* 'Karina', not patented. In side-by-side comparisons conducted in Oudelande, The Netherlands, plants of the new *Papaver* differed from plants of 'Karina' in the following characteristics:

1. Plants of the new *Papaver* were taller than plants of 'Karina'.
2. Plants of the new *Papaver* had stronger stems than plants of 'Karina'.
3. Plants of the new *Papaver* had larger flowers with more petals than plants of 'Karina'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Papaver*.

The photograph on the first sheet is a side perspective view of a typical plant of 'Paradiso' grown in a container.

The photograph at the top of the second sheet is a close-up view of typical flowers of 'Paradiso'.

The photograph at the bottom of the second sheet is a close-up view of a typical leaf of 'Paradiso'.

DETAILED BOTANICAL DESCRIPTION

Plants used for the aforementioned photographs and following description were grown under conditions which closely approximate commercial production conditions during the spring an outdoor nursery in Boskoop, The Netherlands. During the production of the plants, day temperatures ranged from 14° C. to 27° C. and night temperatures ranged from 5° C. to 15° C. Plants used for the photographs and the description were one year from planting. In the following description, color references are made to The Royal Horticultural Society Colour Chart, 2001 Edition, except where general terms of ordinary dictionary significance are used.

Botanical classification: *Papaver orientale* 'Paradiso'.

Parentage:

*Female parent.*—Unnamed selection of *Papaver orientale,* not patented.

*Male parent.*—Unnamed selection of *Papaver orientate,* not patented.

Propagation:

*Type.*—By divisions.

*Time to initiate roots.*—About three weeks at 20° C.

*Time to produce a rooted young plant.*—About six weeks at 20° C.

*Root description.*—Thick, fleshy; brown in color.

*Rooting habit.*—Freely branching.

Plant description:

*Form.*—Herbaceous perennial flowering plant; mostly upright. Basally branching, rosette; flowering stems arise from the base. Moderately vigorous growth habit.

*Plant height.*—About 61.9 cm.

*Plant width.*—About 44.1 cm.

*Branch description.*—Arrangement: Basal branching; about seven basal branches develop per plant. Length: About 54.2 cm. Diameter: About 4 mm. Internode length: About 7.6 cm. Strength: Strong. Aspect: Upright. Texture: Pubescent; rough. Color: Close to 144A.

Foliage description:

*Arrangement.*—Alternate, simple.

*Length.*—About 24.2 cm.

*Width.*—About 8 cm.

*Shape.*—Narrowly ovate; mostly pinnatisect, towards the apex, pinnatifid.

*Apex.*—Broadly acute.

*Base.*—Cuneate.

*Margin.*—Serrate to biserrate.

*Texture, upper and lower surfaces.*—Pubescent; rough.

*Venation pattern.*—Pinnate.

*Color.*—Developing foliage, upper surface: Close to 143A; towards the base, close to 144A. Developing foliage, lower surface: Close to 138A. Fully expanded foliage, upper surface: Close to 137A; venation, close to 145C to 145D. Fully expanded foliage, lower surface: Close to 137C; venation, close to 144B.

*Petiole length.*—About 6.2 cm.

*Petiole diameter.*—About 5 mm by 6 mm.

*Petiole color, upper and lower surfaces.*—Close to 145A.

Flower description:

*Flower arrangement and appearance.*—Large semi-double rotate flowers; flowers terminal and face mostly upright; about seven flowers per plant at one time.

*Natural flowering season.*—Continuous flowering during the late spring in The Netherlands.

*Flower longevity on the plant.*—About three days; flowers not persistent.

*Fragrance.*—None detected.

*Flower buds.*—Length: About 3.1 cm. Diameter: About 2 cm. Shape: Ovate. Texture: Densely pubescent. Color: Close to 137B to 137C.

*Flower diameter.*—About 9.3 cm.

*Flower depth (height).*—About 5.1 cm.

*Petals.*—Arrangement: About six in one to two whorls. Length: About 6.2 cm. Width: About 8.3 cm. Shape: Flabellate. Apex: Retuse. Margin: Entire. Texture, upper and lower surfaces: Smooth, glabrous. Color: When opening and fully opened, upper surface: Close to 43D; towards the margins, close to 38C to 38D; towards the base, spot, between N186C and 202A; at the base, close to 53C. With development, color becoming closer to 38B; towards the margins, close to 38C to 38D; towards the base, close to N186C; at the base, close to 53D. When opening and fully opened, lower surface: Close to 43D; towards the margins, close to 37D; towards the base, spot, close to N186C; at the base, close to 53C.

*Sepals.*—Sepal development has not been observed.

*Peduncles.*—Length: About 19.2 cm. Diameter: About 4 mm. Strength: Strong. Texture: Pubescent; rough. Color: Close to 144A.

*Reproductive organs.*—Stamens: Quantity per flower: About 250. Filament length: About 1.8 cm. Filament color: Close to N186C; towards the base, close to N155B. Anther shape: Oblong. Anther length: About 2.5 mm. Anther color: Close to 202A. Pollen amount: Scarce. Pollen color: Between N186A and 202A. Pistils: Quantity per flower: About twelve. Pistil length: About 8 mm. Stigma shape: Narrowly oblong. Stigma color: Between N79A and 187A. Ovary color: Close to 138A to 138B.

*Fruits.*—Type: Capsule. Quantity per flower: One. Length: About 2.2 cm. Diameter: About 2.2 cm. Color: Close to 137A.

*Seeds.*—Quantity per fruit: About 750. Length: About 1 mm. Diameter: About 1 mm. Color: Close to 202A to 202B.

Disease/pest resistance: Plants of the new *Papaver* have not been noted to be resistant to pathogens and pests common to *Papaver*.

Garden performance: Plants of the new *Papaver* have exhibited good tolerance to rain, wind, and temperatures ranging from about −20° C. to about 40° C.

What it is claimed:

1. A new and distinct *Papaver* plant named 'Paradiso' as illustrated and described.

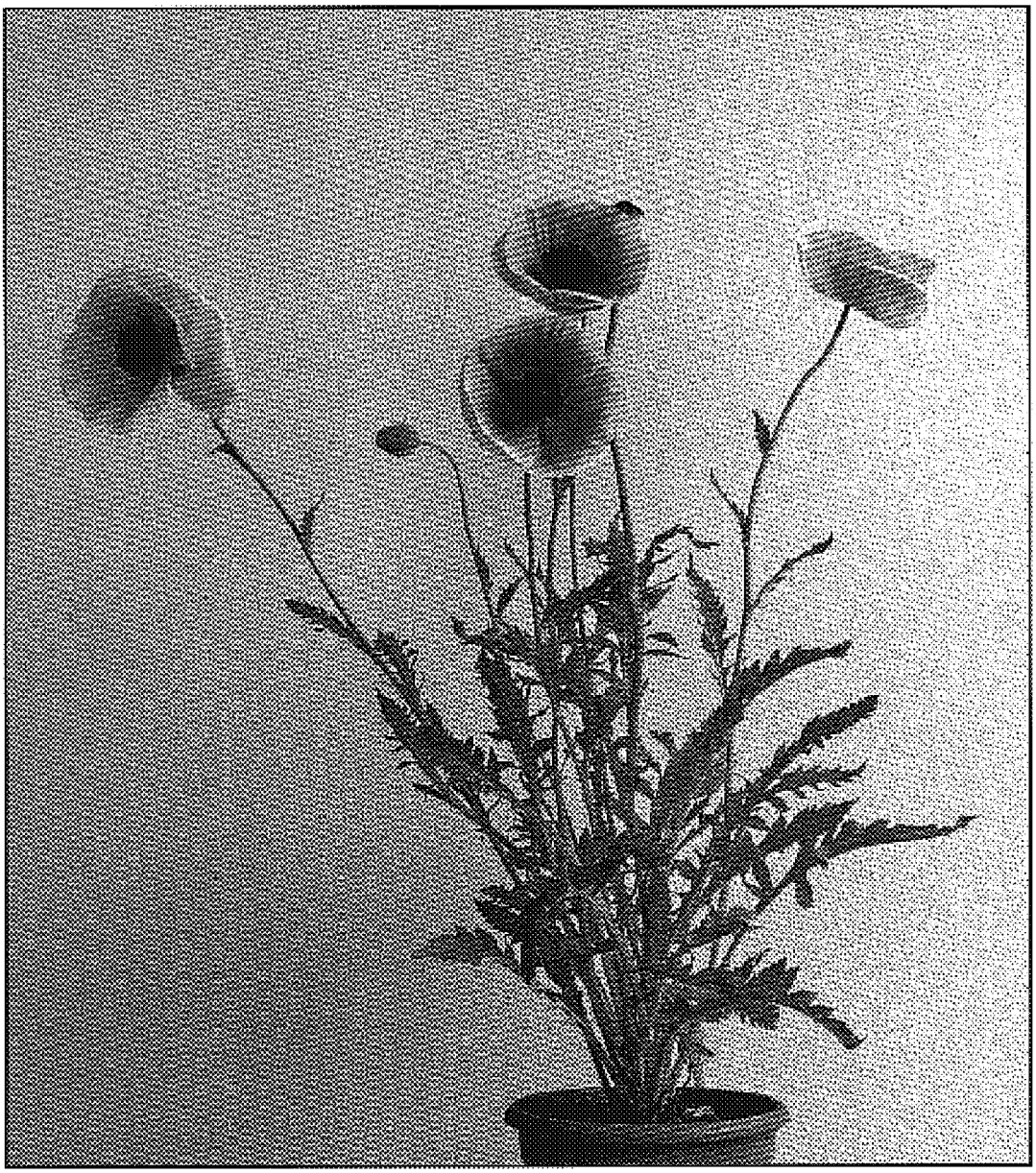

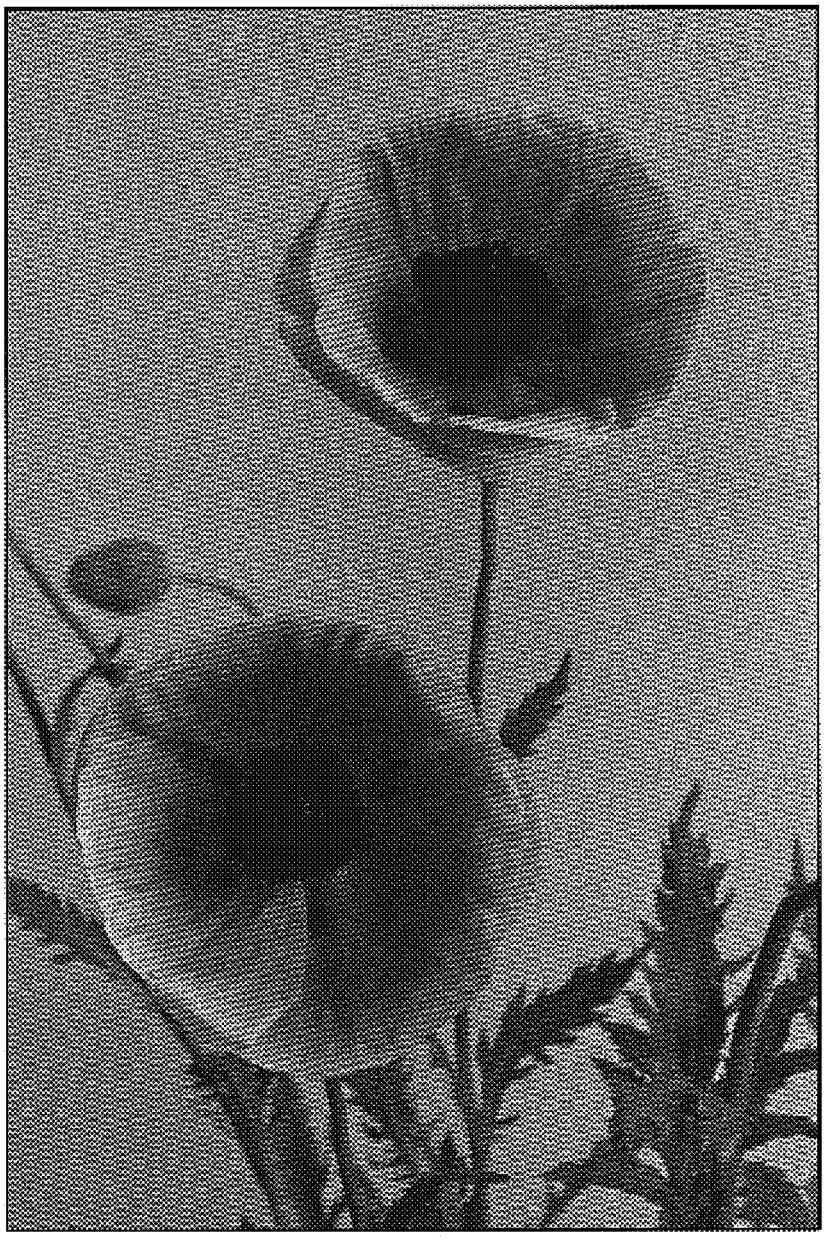
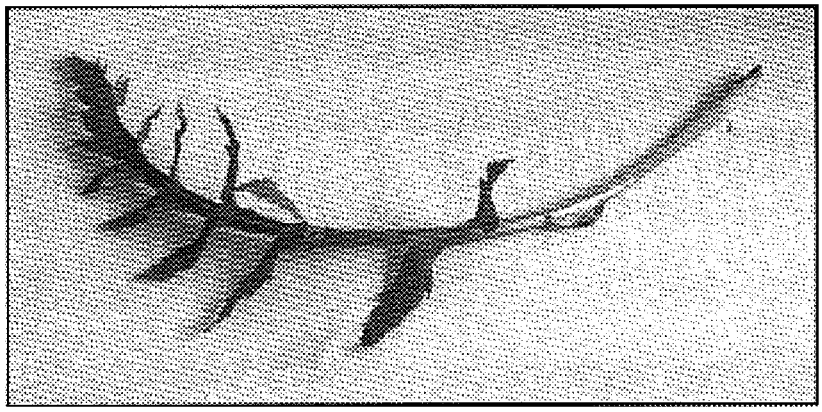

* * * * *